US005801003A

United States Patent [19]
Shimamura et al.

[11] Patent Number: 5,801,003
[45] Date of Patent: Sep. 1, 1998

[54] METHOD AND REAGENT DETECTING HUMAN DISORDERS

[75] Inventors: Toshiro Shimamura; Junji Hamuro, both of Kawasaki; Kazuo Sugamura, Sendai, all of Japan

[73] Assignee: Ajinomoto Co., Inc., Tokyo, Japan

[21] Appl. No.: 568,427

[22] Filed: Dec. 6, 1995

[30] Foreign Application Priority Data

Dec. 6, 1994 [JP] Japan .................................. 6-301837

[51] Int. Cl.$^6$ .......................... C12Q 1/70; G01N 33/53; G01N 33/543; G01N 33/574
[52] U.S. Cl. .................. 435/7.23; 435/7.24; 435/7.92; 435/7.94; 435/5; 436/518
[58] Field of Search ................... 435/7.1, 7.21, 435/7.24, 7.92, 7.94, 5, 7.23; 530/388.1, 388.2, 388.22, 388.23; 436/536, 518

[56] References Cited

U.S. PATENT DOCUMENTS 4,707,443  11/1987  Nelson et al. .
5,006,459  4/1991   Kung et al. .

FOREIGN PATENT DOCUMENTS 0 526 952   2/1993   European Pat. Off. .
0 578 932   1/1994   European Pat. Off. .
0 621 338   10/1994  European Pat. Off. .
WO 90/05303  5/1990  WIPO .
WO 96/01122  1/1996  WIPO .

OTHER PUBLICATIONS

Motoi et al. (1988) JPn. J. Cancer Res. vol. 79:593–599.
Rubin et al. (1985) J. Immunol. vol. 135, No. 5: 3172–3177.
Kondo et al. (1993) Tissue antigens 42(4) : 342.

Science, vol. 262, pp. 1874–1877, Dec. 17, 1993, Motonari Kondo, et al., "Sharing of the Interleukin-2 (IL-2) Receptor γ Chain Between Receptors for IL-2 and IL-4".

Science, vol. 257, pp. 379–382, Jul. 17, 1992, Toshikazu Takeshita, et al., "Cloning of the γ Chain of the Human IL-2 Receptor".

J. Exp. Med., vol. 180, pp. 241–251, Jul. 1994, Takayuki Nakarai, et al., "Interlukin 2 Receptor γ Chain Expression on Resting and Activated Lymphoid Cells".

J. Exp. Med., vol. 176, pp. 531–541, Aug. 1992, Stephen D. Voss, et al., "Characterization of the Interleukin 2 Receptors (IL-2R) Expressed on Human Natural Killer Cells Activated in Vivo by IL-2: Association of the p64 IL-2R γ Chain with the IL-2R βChain in Fuctional Intermediate-Affinity IL-2R".

*Primary Examiner*—Christina Chan
*Assistant Examiner*—Emma Cech
*Attorney, Agent, or Firm*—Oblon, Spivak, McClelland, Maier & Neustadt, P.C.

[57] ABSTRACT

The invention provides a method for detecting (1) leukemia, (2) cancer, (3) autoimmune disorder, (4) inflammatory disorder, (5) allergic disorder or (6) viral infection, characterized by measuring soluble, human interleukin-2 receptor γ-chain molecules existing in a human body fluid by an immunochemical method using an antibody/antibodies specifically reacting with human interleukin-2 receptor γ-chain molecule, and a reagent for the detection.

18 Claims, 1 Drawing Sheet

METHOD AND REAGENT DETECTING HUMAN DISORDERS

BACKGROUND OF THE INVENTION

1. Field of the Invention

The present invention relates to a method for detecting various disorders by measuring soluble, human interleukin-2 receptor γ-chain molecules (IL-2 receptor γ-chain molecules) existing in human body fluids such as blood, urine, synovial fluid, etc. and to a reagent for the detection. In particular, the detecting method of the present invention is useful for detecting leukemia such as typically adult T-cell leukemia (ATL), cancer, autoimmune disorder such as typically rheumatoid arthritis or systemic lupus erythematosus, inflammatory disorder such as typically hepatitis or pancreatitis, allergic disorder or viral infection.

2. Discussion of the Background

Interleukin-2 (IL-2) is a factor extremely important for biophylaxis, which is known to act on various immunocompetent cells in organisms, such as B-cells, natural killer cells and lymphokine-activating killer cells, as well as the proliferation and differentiation of killer T-cells. IL-2 was isolated and its structure determined by one of the present inventors (see Nature, Vol. 302, p. 305, 1983).

The physiological activities of IL-2 is expressed when its effector binds to a IL-2 receptor expressed on the surfaces of cells. Three types of IL-2 receptors are known and are differentiated from one another in their binding affinity with IL-2: (1) high-affinity type ($K_d=10^{11}$/M), (2) intermediate-affinity type ($K_d=10^9$/M) and low-affinity type ($K_d=10^8$/M).

In 1984, a gene for a 55 kD receptor molecule, which is now referred to as α-chain, was cloned (see Nature, Vol. 311, p. 626, 1984; Nature, Vol. 311, p. 631, 1984). In 1989, a gene for a 75 kD receptor molecule, which is now referred to as β-chain, was cloned (see Science, Vol. 244, p. 551, 1989). In 1992, a gene for a 64 kD receptor molecule, which is now referred to as γ-chain, was cloned (see Science, Vol. 257, p. 379, 1992). Based on these receptors, the binding modes of the three IL-2 types were determined. The high-affinity receptor is composed of an α-chain, a β-chain and a γ-chain. The intermediate-affinity receptor is composed of a β-chain and a γ-chain. The low-affinity receptor is composed of α-chains.

Of these three types of IL-2 receptors, the high-affinity receptor and the intermediate-affinity receptor are, after IL-2 binds thereto, taken into cells and serve as triggers for IL-2 signal transduction. IL-2 receptors composed of only α-chain or α-chain and β-chain have no function for IL-2 signal transduction (see Science, Vol. 257, p. 379, 1992). Thus, the γ-chain of IL-2 receptor is indispensable for IL-2 signal transduction.

Among the component molecules of IL-2 receptors, the extracellular region of the α-chain molecule, i.e., a soluble IL-2 receptor α-chain molecule, exists in culture supernatant of a certain T-cell line (J. Immunol., Vol. 135, p. 3172, 1984). Such soluble IL-2 receptor α-chain molecules exist also in human serum, especially in the serum of ATL patients at a high level (see Jpn. J. Cancer Res., Vol. 79, p. 593, 1988). The physiological role of the soluble IL-2 receptor α-chain molecule is not clear at present, but since the molecules exist in ATL patients at a high level, the molecule was expected to be applicable for the diagnosis of ATL.

ATL is a leukemia that is caused by the infection of CD4 antigen-positive T-cells with human T-cell leukemia virus I-type (HTLV-I). It is believed that the disease progresses by a so-called autocline mechanism where HTLV-I proviruses are taken into the gene for the host T-cell, then the transcription of IL-2 and IL-2 receptor genes is promoted, and the IL-2 thus produced binds to the expressed IL-2 receptor, to be continuously propagated (see Blood, Vol. 72, p. 1805, 1988).

As the γ-chain molecule among the component molecules of the IL-2 receptor is indispensable for IL-2 signal transduction, the measurement of the γ-chain molecules of IL-2 receptor is more functional than that of the α-chain molecules and that the former is more practicable than the latter for the diagnosis of ATL. In fact, HTLV-I-infected cell lines MT-I and MT-2 strongly express the messenger RNA for IL-2 receptor γ-chain (see Science, Vol. 257, p. 379, 1992). Thus, IL-2 receptor γ-chain molecules may be used to index for the symptoms of ATL.

However, only the gene sequence for the IL-2 receptor γ-chain molecule is known, and it is unclear as to whether or not IL-2 receptor γ-chain molecules are expressed in the surfaces of ATL patients' cells, let alone as to whether or not soluble IL-2 receptor γ-chain molecules exist in human body fluids like IL-2 receptor α-chain molecules. Furthermore, the relationship between soluble IL-2 receptor γ-chain molecules and various disorders such as ATL is quite unclear.

SUMMARY OF THE PRESENT INVENTION

Accordingly, one object of the present invention is to provide a method for detecting various disorders, for example, leukemia such as typically ATL, by measuring the amount of soluble IL-2 receptor γ-chain molecules existing in human body fluids such as blood, urine, synovial fluid, etc., at high sensitivity and with accuracy and simplicity.

The present inventors have now found that soluble IL-2R γ-chain molecules do indeed exist in human biological fluids. Further, the present inventors have formed a multiplicity of monoclonal antibodies specific to human IL-2 receptor γ-chain molecules. This is the first system for measuring soluble IL-2 receptor γ-chain molecules existing in a human body fluid at high sensitivity and with accuracy and simplicity, by measuring the amount of soluble, human IL-2 receptor γ-chain molecules as bonded to such a monoclonal antibody specific to human IL-2 receptor γ-chain molecules by use of a sandwich immunoassay method using the combination of such antibodies and surface plasmon resonance.

Using the measuring system of the invention, the present inventors have demonstrated that soluble IL-2 receptor γ-chain molecules exist in human blood and that soluble IL-2 receptor γ-chain molecules exist in the blood of patients with ATL, hepatitis or pancreatitis at high levels. On the basis of these findings, the present inventors have established a method for detecting various disorders, for example, leukemia such as typically ATL, by measuring such soluble IL-2 receptor γ-chain molecules existing in a human body fluid and have also completed a reagent for the detection.

DETAILED DESCRIPTION OF THE PREFERRED EMBODIMENTS

Figure 1:
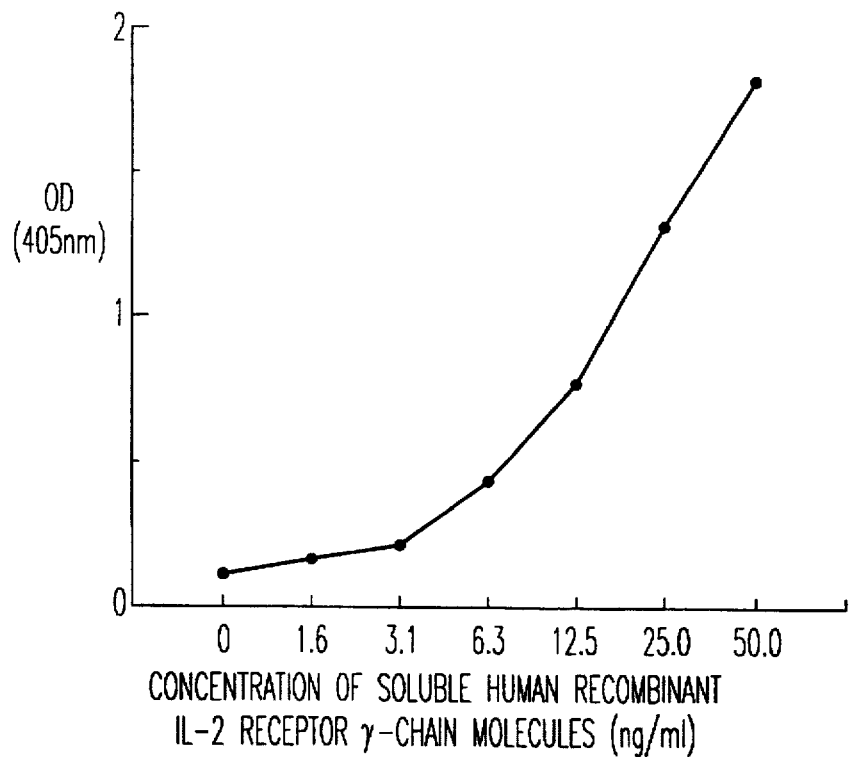
FIG. 1 shows the results of the measurement of soluble human IL-2 receptor γ-chain molecules using a sandwich enzyme immunoassay.

The present invention provides a method for detecting leukemia, cancer, autoimmune disorder, inflammatory disorder, allergic disorder or viral infection, which comprises contacting a human biological fluid with an antibody specific for human interleukin-2 receptor (IL-2R) γ-chain molecules so as to form a complex of said antibody with any IL-2R γ-chain molecules in said fluid, and measuring the amount of complex.

Suitable monoclonal antibodies for use in the present invention can be obtained, according to ordinary methods, by immunizing animals with human IL-2 receptor γ-chain molecules or with human IL-2 receptor γ-chain-expressing cells, fusing the resulting antibody-producing cells and myeloma cells, selecting the resulting hybridomas that produce monoclonal anti-human IL-2 receptor γ-chain antibodies, cultivating the thus-selected hybridomas, and collecting the thus-produced monoclonal antibodies.

Suitable hybridomas can be produced by fusing myeloma cells and antibody-producing cells. Preferred antibody-producing cells include cells of the spleen or lymphonodus of animals, such as mice, rats, etc. which have been immunized with recombinant human IL-2 receptor γ-chain molecules. Preferred immunizing substances include recombinant human IL-2 receptor γ-chain molecule used singly or as a fusion molecule with other proteins. Peptide fragments of human IL-2 receptor γ-chain molecules can also be used. Of these, a peptide composed of only extracellular region of the human IL-2 receptor γ-chain molecule is especially effective. In place of recombinant human IL-2 receptor γ-chain molecule, human cells that express human IL-2 receptor γ-chain molecule, mouse cells with a gene coding for a human IL-2 receptor γ-chain molecule as introduced thereinto to thereby produce the γ-chain molecule by biosynthesis, etc., can also be used. Human IL-2 receptor γ-chain molecule obtained by purification of such cells can also be used as immunogen.

The species of the animals from which the antibody-producing cells and the myeloma cells are derived may be different provided that the cells are fusable together, but in general, cells derived from the same species are normally used to obtain favorable results. One preferred embodiment of the hybridoma to be used for carrying out the present invention is a hybridoma produced by fusing spleen cells or lymphonodus cells of mice as immunized with soluble, human recombinant IL-2 receptor γ-chain molecule composed of only the extracellular region of human recombinant IL-2 receptor γ-chain molecule, and mouse myeloma cells.

Particularly preferred is a hybridoma produced by fusing spleen cells of a Balb/c mouse as immunized with soluble, human recombinant IL-2 receptor γ-chain molecule, which is suspended in a physiologically saline solution, and myeloma cells SP2/0-Ag14 of a Balb/c mouse. As shown in the following examples, favorable results were obtained with the hybridoma.

Soluble, human recombinant IL-2 receptor γ-chain molecule can be obtained by cultivating transformants having an expression plasmid vector containing a gene coding for the molecule. Suitable transformants include any of prokaryotic cells such as *E. coli* cells, etc. and eukaryotic cells such as CHO cells, NIH3T3 cells, etc.

Suitable myeloma cells include those of 8-azaguanine-resistant cell strains, such as X63-Ag8-6.5.3, P3-X63-Ag8-UI, P3-X63-Ag8, P3-NSI/1-Ag4-1 and MPC11-4.5.6.TG.1.7 (all of mouse cells), 210.RCY.Ag1.2.3 (of rat cells), SK0-007 and GH15006TG-A12 (both of human cells), etc., in addition to SP2/0-Ag14 mentioned above.

The preparation of hybridomas and the screening thereof to select hybridoma clones that produce monoclonal antibodies having the activity to bond to human IL-2 receptor γ-chain molecule can be conducted using techniques known in the art. For example, antibody-producing cells and myeloma cells are fused together, using polyethylene glycol or Sendai virus or the like. Only the fused hybridomas can grow in a medium containing hypoxanthine, thymidine and aminopterin (HAT medium). Since all of the thus-obtained hybridomas do not always produce antibodies and since all of the hybridomas that produce antibodies are not always ones that produce the intended antibodies, these hybridoma clones must be screened to select therefrom those that produce monoclonal antibodies having the activity to bind to human IL-2 receptor γ-chain molecules.

Screening can be conducted, for example, by determining the presence or absence of the bonding of the antibodies as produced in the culture supernatant of the hybridomas to human IL-2 receptor γ-chain molecules by radioimmunoassay, enzyme immunoassay or the like.

The preparation of monoclonal antibodies from the thus-obtained hybridomas that produce antibodies to human IL-2 receptor γ-chain molecule can be conducted by inoculating the hybridomas into the peritoneal cavity of histocompatible animals, thymus-deleted nude mice or the like, propagating them therein, collecting the antibodies produced in the ascites of the animals, and purifying them by salting-out, ion-exchange chromatography or the like.

The quantitative determination of human IL-2 receptor γ-chain molecules according to the immunochemical method of the present invention may be conducted as follows:

For the determination by a sandwich method, two monoclonal anti-human IL-2 receptor γ-chain antibodies which are specific to different epitopes, as produced in the manner mentioned above, are prepared. The first anti-human IL-2 receptor γ-chain antibody of the two is fixed to a solid phase, such as the inner wall of each well in a micro-titer plate. Its non-specific adsorptive sites are blocked with bovine serum albumin (BSA) or the like. Then this is reacted with a sample to be tested and washed. Thereafter this is reacted with the second monoclonal anti-human IL-2 receptor γ-chain antibody and washed. The amount of the second antibody bonded to the solid phase can be measured to quantitatively determine the soluble human IL-2 receptor γ-chain molecules in the sample.

The measurement of the amount of the second antibody can be conducted by various methods well-known in the field of immunoassay. As one example, the second antibody is previously labeled with an enzyme, and a color-developing substrate or a chemiluminescent substrate is applied thereto. As another example, biotin is previously conjugated to the second antibody, this is reacted with a labeled avidin, and the degree of the labeling of the resulting reaction product is measured. As still another example, the second antibody is further reacted with a labeled antibody specifically reactive with the second antibody, and the degree of the labeling of the resulting reaction product is measured. To label the second antibody, also usable is any of fluorescent dyes and radioactive substances in place of enzyme.

Any monoclonal antibodies which are specifically reactive with human IL-2 receptor γ-chain molecule can be used herein, provided that they are specific to different epitopes. Polyclonal antibodies are also usable.

Alternatively the quantitative determination can be conducted using sufrace plasman resonance. A monoclonal anti-human IL-2 receptor γ-chain antibody of the present invention is chemically fixed onto carboxymethyldextran that has been bonded to the surfaces of glass/metal chips. Then, a sample to be tested is applied thereto, reacted therewith and washed. Therefore, the degree of surface plasmon resonance which occurs after light is applied to the reaction system is measured. The amount of the bonded IL-2 receptor γ-chain molecules can be quantitatively determined. Surface plasmon resonance has been described in Physics of Thin Films, vol. 9, pp. 145–261, Academic Press New York, 1977 and J. Biomolecular Interactions, "Kinetic Analysis Using BIA", Pharmacia Biosensor AB, 1994.

Among the multiplicity of monoclonal anti-human IL-2 receptor γ-chain antibodies thus formed according to the methods mentioned hereinabove, most preferred one in the sandwich method is a combination of AG43 (the hybridoma cell line producing this monoclonal antibody has been deposited in accordance with the Budapest treaty in the National Institute of Bioscience Human Technology, Agency of Industrial Science and Technology, Ministry of International Trade and Industry, 1–3, Higashi 1-chome, Tsukuba-shi, Ibaraki-ken 305, Japan, on Nov. 20, 1995, under deposition number of FERM BP-5296) as the first antibody and TUGh5 (the hybridoma cell line producing this monoclonal antibody was likewise deposited in accordance with the Budapest Treaty in the National Institute of Bioscience and Human Technology, Agency of Industrial Science and Technology, Ministry of International Trade and Industry, 1–3, Higashi 1-chome, Tsukuba-shi, Ibaraki-ken 305, Japan, on Apr. 16, 1995, under deposition number of FERM BP-4643) as the second antibody, with which soluble human IL-2 receptor γ-chain molecules were measured at the highest sensitivity. In the method of measuring the bonded, soluble human IL-2 receptor γ-chain molecules by means of surface plasmon resonance, AG43 is most preferably used as the monoclonal anti-human IL-2 receptor γ-chain antibody to be in a fixed phase, with which soluble human IL-2 receptor γ-chain molecules were measured at the highest sensitivity.

The sample to be tested according to the present invention includes various human-derived body fluids, such as serum, blood, urine, etc.

The antibodies for use in the measuring method of the present invention are not limited to the above-mentioned monoclonal anti-human IL-2 receptor γ-chain antibodies. The antibodies for use in the measuring method of the present invention may be antibodies themselves but may also be their F(ab)'2 fragments or Fab fragments as cleaved with enzymes, or antibodies where the C regions of the H chains and the L chains have been converted to human-type ones by genetic engineering, or antibodies where the C regions of the H chains and the L chains have been deleted to give single-stranded antibodies with peptide linkers, or antibodies to which enzymes have been bonded by genetic engineering.

Again, the present invention provides a reagent for detecting leukemia, cancer, autoimmune disorder, inflammatory disorder, allergic disorder or viral infection, which comprises an antibody/antibodies specifically reacting with human interleukin-2 receptor γ-chain molecule and with which are measured soluble, human interleukin-2 receptor γ-chain molecules existing in a human body fluid by an immunochemical method.

Since the expression of IL-2 receptor γ-chain is observed to be promoted in the local site of cancer in terminal cancer-carrying patients, the measuring method of the invention can also be the method for determining the degree of the promotion of cancer. Furthermore, it is also applicable to the detection of autoimmune disorder, such as rheumatoid arthritis or systemic lupus erythematosus, and allergic disorder, of which the presentation of the symptoms is deeply related to abnormal activation of T-cells.

The reagent is used according to the detecting methods mentioned hereinabove. The antibodies to be used in the reagent are also such monoclonal antibodies as those mentioned hereinabove.

EXAMPLES

Having generally described this invention, a further understanding can be obtained by reference to certain specific examples which are provided herein for purposes of illustration only and are not intended to be limiting unless otherwise specified.

Example 1
Preparation of Soluble, Recombinant Human IL-2 Receptor γ-chain Molecule Composed of Only Extracellular Regions To prepare a human IL-2 receptor γ-chain cDNA having a stop codon at the 3'-terminal in the extracellular region, an oligomer 5'-GGACATATGCTGAACACGACAATTCTG-3' (SEQ ID NO:1) having an NdeI site in the inside and an oligomer 5'-GAAAAGCTTCTATTATGAAGTATTGCTCC-3' (SEQ ID NO:2) having an HindIII site in the inside were synthesized with a DNA synthesizer (Applied Biosystems Co. Inc.). Both oligomers as primers and a plasmid containing a cDNA for a human IL-2 receptor γ-chain molecule (*E. coli* as transformed with this plasmid has been deposited in the National Institute of Bioscience and Human Technology, Agency of Industrial Science and Technology, Ministry of International Trade and Industry, 1–3, Higashi 1-chome, Tsukuba-shi, Ibaraki-ken 305, Japan, under deposit number FERM BP-4200) as a template, were subjected to PCR with a Taq polymerase, using a thermal cycler (denaturation at 94° C., annealing at 55° C. and synthesis at 72° C., for 20 cycles). The cDNA structure of a human IL-2 receptor γ-chain molecule is disclosed in European Patent Application Laid-Open No. EP-0578932 based on the EPC treaty, Science, Vol. 257, p. 379, 1992, etc. and is hereby incorporated herein by reference.

An amplified band of about 0.7 kb was recovered and cut with NdeI and HindIII (ex Takara Shuzo), and then ligated with a large fragment of plasmid pFv(TU27)-DE (*E. coli* as transformed with this plasmid has been deposited in the National Institute of Bioscience and Human Technology, Agency of Industrial Science and Technology, Ministry of International Trade and Industry, 1–3, Higashi 1-chome, Tsukuba-shi, Ibaraki-ken 305, Japan, as a deposition number of FERM BP-3973) that had been cut with NdeI and HindIII and recovered, thereby to construct a plasmid pIL-2RGS.

*E. coli* HB101 as transformed with the plasmid pIL-2RGS was cultivated in an M9-Casamino acid medium, whereby granules were produced in the cells of the *E. coli*. The *E. coli* cells were ultrasonically pulverized and centrifuged at 3,000×g to thereby separate the granules. Next, the granules were dissolved in 6M guanidine hydrochloride, then stirred overnight at room temperature in the presence of 3.5M of guanidine hydrochloride, 30 μM glutathione (reduced form) and 3 μM glutathione (oxidized form) as the final concentration under the condition of a protein concentration of 50 μg/ml, for rewinding, and subjected to dialysis against a 10 mM phosphate buffer (pH 7.5) containing 150 mM NaCl PBS to prepare soluble, recombinant human IL-2 receptor γ-chain molecules.

Example 2
Preparation of Hybridomas

Female BALB/c mice of from 6 to 8 week-age were immunized by subcutaneously administering thereto 100 μg/mouse of the soluble, recombinant human IL-2 receptor γ-chain molecules along with a Freund's complete adjuvant (Bacto Co. Inc.). Additional immunization of the mice was repeated two times by the same treatment as above at intervals of 3 weeks. The blood was collected from the supraorbital vein of each mouse, and the amounts of the antibodies as bonded to the soluble, recombinant human IL-2 receptor γ-chain molecule in the blood was measured according to the method described in Example 3 mentioned hereinunder, from which the antibody titer of the blood was determined. The mice having a high antibody titer were finally immunized according to the same treatment as above. After 3 days, the spleen was taken out from each mouse, the spleen cells were mixed and fused with mouse myeloma cells (SP2/0-Ag14) in the presence of 50% polyethylene glycol #4000 (Nacalai Tesque Co., Inc.) at a ratio by number of 10:1.

The fused cells were suspended in an RPMI 1640 medium (Nikken Biomedicine Co., Inc.) containing 10% fetal calf serum (Biocell Co., Inc.) at a concentration of $5 \times 10^6$ cells/ml, and 100 μl of the resulting cell suspension was put into each well of a 96-well flat-bottom plate (Corning Co., Inc.) containing $5 \times 10^5$ mouse thymocytes. After 1, 2, 3 and 6 days, a half of the medium was exchanged for a medium containing hypoxanthine, aminopterin and thymidine (HAT medium), and thereafter the same operation was repeated every three days. About 2 weeks after the cell fusion, the presence or absence of the binding of the antibodies contained in the supernatant from the culture in each well where the fused cells (hybridomas had grown, to the soluble, recombinant human IL-2 receptor γ-chain molecules was checked, and the hybridomas in the culture supernatant samples exhibiting the intended binding were cloned according to a limiting dilution-culture method.

Again in the same manner as above, the amounts of the antibodies as bonded to the cells in the culture supernatant from each hybridoma clone were measured, according to which anti-IL-2 receptor γ-chain antibody-producing hybridomas were obtained. As the monoclonal anti-human IL-2 receptor γ-chain antibodies thus obtained, there are AG43 and TUGh-5.

Example 3
Measurement of the Binding Ability of the Antibodies Contained in an Anti-serum and a Culture Supernatant to Human IL-2 Receptor γ-chain Molecule 50 μl of a suspension of the soluble recombinant human IL-2 receptor γ-chain molecule, which had been prepared in Example 1 and had been suspended in 0.1M carbonate buffer (pH 9.6) at a concentration of 2 μg/ml, was put into each well of a 96-well flat-bottom plate (Flow Co., Inc.) and was left therein overnight at 4° C., whereby the molecules were adsorbed to each well. Next, the suspension was removed, and 200 ml of a PBS solution containing 0.5% bovine serum albumin (Biocell Co., Inc.) was put into each well and was left therein for 2 hours as it was at room temperature. Next, the solution was removed and 50 μl of a diluted anti-serum sample or a hybridoma culture supernatant sample was added to each well and reacted with the molecules for 2 hours at room temperature. Each well was washed with PBS containing 0.05% TWEEN 20 (PBS-TWEEN) three times, and 50 μl of a solution of an alkali phosphatase-labeled anti-mouse immunoglobulin (Cappel Co., Inc.) was added to each well and reacted for 2 hours at room temperature. Each well was washed with PBS-TWEEN three times and 50 μl of a solution of paranitrophenol phosphate (Sigma Co., Inc.) having a concentration of 1 mg/ml by adjustment of 50 mM carbonate buffer (pH 9.8) was added to each well and left at room temperature for 15 minutes. After this, the absorbance at 405 nm of the sample in each well was measured, using an immunoreader (Biorad Co., Inc.), from which was determined the binding ability of the antibodies in the sample to the IL-2 receptor γ-chain molecule.

Example 4
Preparation of Standard Samples of Soluble Human IL-2 Receptor γ-chain Molecule As standard sample of soluble human IL-2 receptor γ-chain molecule, used was recombinant expressed in NIH3T3 cell. The recombinant was prepared in the manner mentioned below.

To prepare an IL-2 receptor γ-chain cDNA having a stop codon at the 3'-terminal in the extracellular region, an oligomer 5'-GAAGAGCTCGAGCGCCATGTTGAAGCCAT-3' (SEQ ID NO:3) having an XhoI site in the inside and an oligomer 5'-GAAAAGCTTCTATTATGAAGTATTGCTCC-3' (SEQ ID NO:2) having a HindIII site in the inside were synthesized with a DNA synthesizer. The both oligomers as primers and a plasmid containing a cDNA for a human IL-2 receptor γ-chain molecule (E. coli as transformed with this plasmid has been deposited in the National Institute of Bioscience and Human Technology, Agency of Industrial Science and Technology, Ministry of International Trade and Industry, 1-3, Higashi 1-chome, Tsukuba-shi, Ibaraki-ken 305, Japan, as a deposition number of FERM BP-4200) as a template, were subjected to PCR with a Taq polymerase, using a thermal cycler (denaturation at 94° C., annealing at 55° C. and synthesis at 72° C., for 20 cycles).

An amplified band of about 0.7 kb was recovered and cut with XhoI (Takara Shuzo Co., Inc.) and HindIII. Next the resultant fragment was ligated with the fragment which had cut pBluescriptII (Stratagene Co., Inc.) with XhoI and HindIII and then had recovered. After that, this was cut with XhoI and NotI (Takara Shuzo Co., Inc.) and then ligated with a BCMGNeo vector (see Experimental Medicine, Separate Volume, Genetic Engineering Handbook, p. 297, 1991, published by Yodo Publishing) that had been previously cut with XhoI and NotI and recovered, to thereby construct a vector having an extracellular region cDNA of an IL-2 receptor γ-chain molecule as inserted thereinto.

Next, the vector obtained thus was introduced into NIH3T3 cells according to a calcium phosphate precipitation method (see Greene Publishing Associates and Wiley-Interscience, Current Protocols in Molecular Biology, Chap. 9, Precisely, 10 ml/dish of a suspension of NIH3T3 cells suspended in D-MEM containing 10% fetal calf serum, at a concentration of $1 \times 10^5$ cells/ml, was put into 10-cm laboratory dishes (Falcon Co., Inc.) and incubated overnight at 37° C. in a $CO_2$ incubator. The culture supernatant was removed, and 9 ml of a fresh D-MEM (Nikken Biomedicine Co., Inc.) containing 10% fetal calf serum (Biocell Co., Inc.) was added to each dish, which was further incubated in the $CO_2$ incubator at 37° C. for 2 hours. 30 μg of the vector DNA prepared in the manner mentioned hereinabove was dissolved in 1350 μl of water, 150 μl of 2.5M calcium chloride was added thereto, and the resulting mixture was dropped into a tube containing 1.5 ml of 50 mM Hepes buffer (pH 7.05) containing 280 mM sodium chloride and 1.5 mM disodium monohydrogen phosphate. After immediately mixed, the resulting mixture was left at room temperature for 20 minutes to form a precipitate therein. Next, the precipitate was suspended and one ml of the suspension was added to each laboratory dish where the cells were being incubated, using a Pasteur pipette. After incubated for further 4 hours, the culture supernatant was removed, and 2 ml of D-MEM containing 10% glycerol was added to each dish and left at room temperature for 3 minutes. Then, 5 ml of PBS was added to each dish to dilute the culture therein, each dish was washed with PBS two times, and 10 ml of D-MEM containing 10% fetal calf serum was added thereto and incubated for further 3 days in the $CO_2$ incubator at 37° C.

After this, the medium was exchanged for D-MEM containing 300 µg/ml of G418 (Gibco BRL Co., Inc.) and 10% fetal calf serum, and the incubation was continued further. Then, the colonies formed were separated to obtain clones.

Each clone was incubated, and a total RNA was prepared from about $1\times10^6$ cells, using an Isogene (Nippon Gene Co., Inc.). This was blotted on a nylon membrane (Micron Separation Co., Inc.), using a dot-blotting device (Biorad Co., Inc.). The thus-blotted membrane was dipped in 50% formaldehyde, 5-fold Denhardt's solution, 0.1% SDS and 5-fold SSPE solution, and a CDNA fragment of 0.7 kb, which corresponds to the extracellular region of the above-mentioned human IL-2 receptor γ-chain molecule and which had been labeled with $32_p$ by the use of a random primer labeling kit (Takara Shuzo Co., Inc.), was added thereto and reacted overnight at 42° C. This was washed with 2-fold SSC solution two times and then once with 2-fold SSC solution containing 0.1% SDS, and the amount of the bonded $32_p$-labeled DNA fragment was measured by the use of a bio-image analyzer (Fuji Film Co., Inc.). From the data, obtained were clones having a high bonding value or, that is, clones expressing a large amount of the extracellular region mRNA of human IL-2 receptor γ-chain.

Soluble, human IL-2 receptor γ-chain molecule were prepared from the thus-obtained NIH3T3 cells having an extracellular region cDNA of human IL-2 receptor γ-chain introduced thereinto, in the manner as mentioned below. First, the cells were incubated in D-MEM containing 10% fetal calf serum, which was exchanged for D-MEM containing 2% fetal calf serum at the confluent stage, and these were incubated for further 3 days. 5 liters of the culture supernatant was passed through an AG43 antibody-bonded Sepharose column that had been previously prepared (where 2 mg, per ml of beads, of the antibody was immobilized to beads), washed with PBS and then eluted with 3M NaSCN. The eluate was dialyzed overnight against PBS at 4° C., and soluble human IL-2 receptor γ-chain molecule which can be used as standard samples was obtained.

Example 5
Labeling with Biotin of Monoclonal Anti-human IL-2 Receptor γ-chain Antibody Two monoclonal anti-human IL-2 receptor γ-chain antibodies that had been prepared in Example 2 were labeled with biotin in the manner mentioned below.

First, a solution of each antibody that had been prepared to have a concentration of 200 µg/ml was dialyzed overnight against 0.1M carbonate buffer (pH 8.0) at 4° C. Next, 40 µl of a solution of D-biotin-N-hydroxysuccinimide ester (Behrlinger Manheim Co., Inc.), which solution is adjusted to a concentration of 2 mg/ml by DMSO, was added to 1 ml of the antibody solution and reacted at room temperature for 3 hours. Immediately after the reaction, this was dialyzed overnight against PBS at 4° C. to prepare a biotin-labeled monoclonal anti-human IL-2 receptor γ-chain antibody.

Example 6
Examination of Monoclonal Anti-human IL-2 Receptor γ-chain Antibodies to Check the Sameness or Difference in the Recognition Epitope The two monoclonal anti-human IL-2 receptor γ-chain antibodies prepared in Example 2 were examined as to whether or not they are different from each other in the recognition epitope on human IL-2 receptor γ-chain molecule, in the manner mentioned below.

First, 50 µl of a solution of each monoclonal anti-human IL-2 receptor γ-chain antibody dissolved in 0.1M carbonate buffer (pH 9.6) at a concentration of 10 µg/ml was put in each well of a 96-well flat-bottom plate and left at 4° C. overnight, whereby the antibody was adsorbed to each well. Next, the solution was removed, and 200 µl of a PBS solution containing 0.5% bovine serum albumin was added to each cell and left at room temperature for 2 hours. Then, the solution was removed, and 50 µl of a suspension of the soluble human IL-2 receptor γ-chain molecules that had been prepared in Example 4 and suspended in PBS at a concentration of 100 µg/ml was added to each well and reacted at room temperature for 2 hours. Each well was washed with PBS containing 0.05% TWEEN 20 (PBS-TWEEN) three times, and 50 µl of a solution of either of the two biotin-labeled monoclonal anti-human IL-2 receptor γ-chain antibodies that had been prepared in Example 5 and dissolved in PBS at a concentration of 5 µg/ml was added to each well and reacted for 2 hours at room temperature. Each well was washed with PBS-TWEEN three times, and 50 µl of a solution of paranitrophenol phosphate adjusted to a concentration of 1 mg/ml by use of 50 mM carbonate buffer (pH 9.8) was added to each well and left at room temperature for 15 minutes. After this, the absorbance at 405 nm of the sample in each well was measured, using an immunoreader.

The results are in Table 1. Table 1 shows the results of the tests for the combination of AG43 antibody and TUGh5 antibody. From these results, it is known that the AG43 antibody and the TUGh5 antibody are different from each other in the recognition epitope on IL-2 receptor γ-chain molecule.

TABLE 1

| Labeled | Fixed Antibodies | |
|---|---|---|
| Antibody | AG43 | TUGh5 |
| AG43 | 0.044 | 1.555 |
| TUGh5 | 0.690 | 0.072 |

Example 7
Measurement of Soluble Human IL-2 Receptor γ-chain Molecules by Sandwich Enzyme Immunoassay Soluble human IL-2 receptor γ-chain molecules were measured in the manner mentioned below, according to sandwich enzyme immunoassay using two monoclonal anti-human IL-2 receptor γ-chain antibodies.

First, 50 µl of a solution of AG43 antibody which is adjusted to a concentration of 10 µg/ml by use of 0.1M carbonate buffer (pH 9.6) was put into each well of a 96-well flat-bottom plate and left overnight at 4° C., whereby the antibody was adsorbed to each well.

Next, the solution was removed, and 200 µl of a PBS solution containing 0.5% bovine serum albumin was added to each well and left at room temperature for 2 hours. The solution was removed, and a suspension of the soluble human IL-2 receptor γ-chain molecule that had been prepared in Example 4 and suspended in PBS at a varying concentration was added to each well and reacted at room temperature for 2 hours. Each well was washed with PBS containing 0.05% TWEEN 20 (PBS-TWEEN) three times, and 50 µl of a solution of biotin-labeled TUGh5 antibody which is adjusted to a concentration of 5 µg/ml by PBS was added to each well and reacted for 2 hours at room temperature. Each well was washed with PBS-TWEEN three times, and 50 µl of a solution of paranitrophenol phosphate which is adjusted to a concentration of 1 mg/ml by 50 mM carbonate buffer (pH 9.8) was added to each well and left at room temperature for 15 minutes. After this, the absorbance at 405 nm of the sample in each well was measured, using an immunoreader. FIG. 1 shows the standard curve. As is known from this curve, the sensitivity of the measurement system of this example is 1.6 ng/ml.

Figure 2:
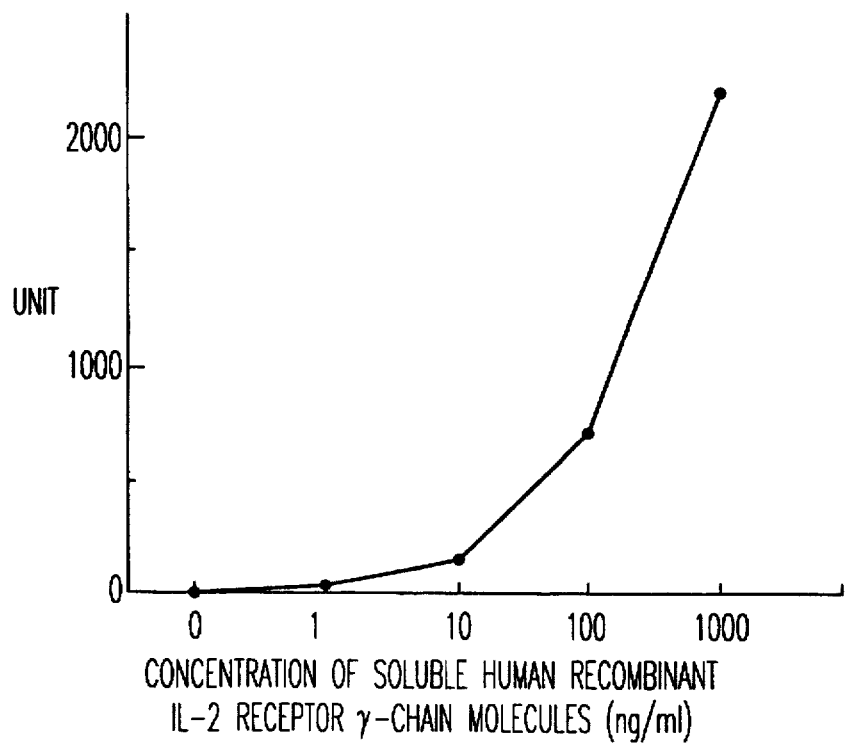
FIG. 2 shows the results of the measurement of soluble human IL-2 receptor γ-chain molecules using surface plasmon resonance.

Example 8
Measurement of Soluble Human IL-2 Receptor γ-chain Molecules by Surface Plasmon Resonance Soluble IL-2 receptor γ-chain molecules were measured by surface plasmon resonance, in the manner mentioned below. First, a solution of AG43 antibody in 10 mM acetate buffer (pH 4.5) having a concentration of 50 µg/ml was fixed onto sensor chips (Pharmacia Co., Inc.) with N-hydroxysuccinimide. Soluble human IL-2 receptor γ-chain molecules with varying concentrations that had been prepared according to Example 4 were reacted with the fixed sensor chips, and the amounts of the antibodies bonded to the molecules were measured in terms of the value resulting from surface plasmon resonance (Viscore Pharmacia Co., Inc.). FIG. 2 shows the standard curve. As is shown in this curve, the sensitivity of the measurement system of this example is 1 ng/ml.

Example 9
Measurement of Soluble Human IL-2 Receptor γ-chain Molecules in the Serum Derived From Healthy Persons or Patients According to the methods of Examples 7 and 8, the concentration of soluble IL-2 receptor γ-chain molecules in the serum derived from healthy persons or from patients with various disorders was measured. In Table 2 are shown the results obtained according to the method of Example 8 or, that is, the method utilizing surface plasmon resonance. As is known from these results, soluble IL-2 receptor γ-chain molecules exist even in the serum from healthy persons but exist in the serum from patients with ATL, hepatitis or pancreatitis at significantly high levels. The values measured according to the method of Example 7 or, that is, according to sandwich enzyme immunoassay, indicated almost the same results.

From these, it is suggested that the detecting method of the present invention is extremely excellent as a method for detecting ATL, hepatitis, pancreatitis, etc.

TABLE 2

Measurement of the Concentration of Soluble IL-2 Receptor γ-chain Molecules in the Blood from Healthy Persons or Patients with Various Disorders

| Subjects | Number of subjects | Mean Value (ng/ml) | SD(ng/ml) |
|---|---|---|---|
| Healthy Persons | 8 | 17.8 | 9.2 |
| Patients with ATL | 6 | 121.0 | 62.5 |
| Patients with Hepatitis | 6 | 42.3 | 11.2 |
| Patients with Pancreatitis | 5 | 50.5 | 13.4 |

The present invention has made it possible to measure and quantitatively determine soluble human IL-2 receptor γ-chain molecules. The present inventors have found for the first time that soluble IL-2 receptor γ-chain molecules exist in the human blood. Again, they have found that soluble IL-2 receptor γ-chain molecules exist in the blood of patients with ATL, hepatitis or pancreatitis at high levels.

Accordingly, using the measuring and determining method of the present invention, it is possible to measure soluble human IL-2 receptor γ-chain molecules at high sensitivity and with accuracy and simplicity and it becomes possible to rapidly and accurately detecting and diagnosing ATL, inflammatory disorder such as hepatitis and pancreatitis, allergic disorder, cancer, and autoimmune disorder such as rheumatoid arthritis.

The present application is based on Japanese application 301837/1994, filed on Dec. 6, 1995, the full text of which is incorporated herein by reference.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method for detecting a disease in a human patient, wherein the disease is associated with elevated levels of a human interleukin-2 receptor γ-chain polypeptide in the patient, wherein the method comprises the steps of:
   (a) obtaining a sample of a biological fluid from the patient;
   (b) providing an antibody specific for the polypeptide;
   (c) contacting the sample with the antibody, whereby a complex comprising the polypeptide and the antibody is formed;
   (d) measuring the amount of the complex; and
   (e) detecting the disease when the amount of the complex exceeds a predetermined magnitude.

2. The method of claim 1, wherein the disease is T-cell leukemia.

3. The method of claim 1, wherein the disease is hepatitis.

4. The method of claim 1, wherein the disease is pancreatitis.

5. The method of claim 1, wherein the disease is rheumatoid arthritis.

6. The method of claim 1, wherein the antibody is AG43 and is produced by the hybridoma cell line having the Accession No. FERM BP-5296.

7. The method of claim 1, wherein the fluid is blood.

8. The method of claim 1, wherein the fluid is urine.

9. The method of claim 1, wherein the fluid is synovial fluid.

10. The method of claim 1, wherein the antibody is in an fixed phase.

11. The method of claim 1, wherein the measuring is by surface plasmon resonance.

12. A method for detecting a disease in a human patient, wherein the disease is associated with elevated levels of a human interleukin-2 receptor γ-chain polypeptide in the patient, wherein the method comprises the steps of:
   (a) obtaining a sample of a biological fluid from the patient;
   (b) providing first and second antibodies specific for the polypeptide, wherein the first and second antibodies recognize different epitopes of the polypeptide;
   (c) contacting the sample with the first antibody, whereby a first complex comprising the polypeptide and the first antibody is formed;
   (d) contacting the first complex with the second antibody, whereby a second complex comprising the polypeptide and the first and second antibodies is formed;

(e) measuring the amount of the second complex; and (f) detecting the disease when the amount of the second complex exceeds a predetermined magnitude.

13. The method of claim 12, wherein the disease is T-cell leukemia.

14. The method of claim 12, wherein the disease is hepatitis.

15. The method of claim 12, wherein the disease is pancreatitis.

16. The method of claim 12, wherein the disease is rheumatoid arthritis.

17. The method of claim 12, wherein the first antibody is AG43 and is produced by the hybridoma cell line having the Accession No. FERM BP-5296.

18. The method of claim 12, wherein the second antibody is TUGh5 and is produced by the hybridoma cell line having the Accession No. FERM BP-4643.

* * * * *

UNITED STATES PATENT AND TRADEMARK OFFICE
CERTIFICATE OF CORRECTION

PATENT NO.  : 5,801,003
DATED       : September 1, 1998
INVENTOR(S) : Toshiro SHIMAMURA, et al.

It is certified that error appears in the above-identified patent and that said Letters Patent is hereby corrected as shown below:

On the title page, Item [54], and at the top of column 1, the title is incorrect. It should read:

--METHOD AND REAGENT FOR DETECTING HUMAN DISORDERS--

Signed and Sealed this

Fourth Day of May, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,801,003
DATED : September 1, 1998
INVENTOR(S) : Toshiro SHIMAMURA et al It is certified that error appears in the above-identified patent and that said Letters Patent is hereby corrected as shown below:

Column 4, line 66, "using sufrace plasman" should read --using surface plasman--.

Column 7, line 31, "2 weeks alter the cell" should read --2 weeks after the cell--.

Column 7, line 34, "cells (hybridomas had grown," should read --cells (hybridomas) had grown,--.

Column 9, line 23, "and a CDNA fragment" should read --and a cDNA fragment--.

Column 12, line 10, "detecting and diagnosing" should read --detect and diagnose--.

Signed and Sealed this

Twelfth Day of December, 2000

Attest:

Attesting Officer

Q. TODD DICKINSON

Director of Patents and Trademarks